United States Patent [19]

Primo

[11] 4,125,392

[45] Nov. 14, 1978

[54] SEAWEED EXTRACT PRODUCT AND METHODS OF PRODUCING AND UTILIZING SAME

[76] Inventor: Angelo M. Primo, 35053 Turner, Sterling Heights, Mich. 48077

[21] Appl. No.: 745,171

[22] Filed: Nov. 26, 1976

Related U.S. Application Data

[63] Continuation-in-part of Ser. No. 550,116, Feb. 14, 1975, Pat. No. 4,016,084, and Ser. No. 550,117, Feb. 14, 1975, abandoned.

[51] Int. Cl.² ............................................. A01N 13/00
[52] U.S. Cl. ............................................. 71/3; 71/23; 71/64 G; 71/65; 71/79; 71/DIG. 1; 536/3; 426/2; 426/623; 426/635
[58] Field of Search ............... 426/575, 615, 425, 453, 426/454, 635, 2, 623; 536/3; 71/1, 3, 11, 12, 23, 24, 64 A, 64 G, 65, 79, DIG. 1

[56] References Cited

U.S. PATENT DOCUMENTS

| | | | |
|---|---|---|---|
| 341,072 | 5/1886 | Stanford | 536/3 |
| 598,790 | 2/1898 | Krefting | 536/3 |
| 2,233,787 | 1/1934 | Le Gloahec et al. | 536/3 |
| 2,742,423 | 4/1956 | Saddington et al. | 536/3 |
| 2,877,599 | 3/1959 | Hebestreet et al. | 71/12 |

FOREIGN PATENT DOCUMENTS 27,257 of 1912 United Kingdom ................... 71/23

*Primary Examiner*—Ferris H. Lander
*Attorney, Agent, or Firm*—Irving M. Weiner

[57] ABSTRACT

A seaweed filter cake product produced by conditioning raw seaweed by mixing it with water and other substances, and then digesting the conditioned seaweed by cooking it with steam to form a steam-digested mixture. The filter cake is skimmed off the top of the resulting steam-digested mixture and used by itself, or as a starting product for producing fertilizers or plant growth stimulators in liquid or pelletized form.

42 Claims, No Drawings

SEAWEED EXTRACT PRODUCT AND METHODS OF PRODUCING AND UTILIZING SAME

This application is a continuation-in-part of USSN's 550,116 Now U.S. Pat. No. 4,016,084; and 550,117 now abandoned both filed Feb. 14, 1975.

The invention relates generally to a seaweed filter cake product and methods of producing and using same. In particular, the invention relates to a product produced primarily from fibrous side products which are produced during the production from seaweed of sodium alginate, agar, carrageenin, and a variety of fertilizer products or plant growth stimulators.

The term "filter cake" as used herein is intended to connote skim and tail, alginate pulp, skim cake, agar pulp, carrageenin pulp, and other fibrous material obtained from seaweed, and where all of the foregoing substances and material contain little or no alginic acid.

BACKGROUND OF THE INVENTION

The prior art is exemplified by U.S. Pat. Nos. 103,085; 118,987; 950,455; 1,212,196; 2,075,768; 2,523,626; 2,877,599; 2,940,942; 3,050,424; 3,630,710; 3,649,239; and 3,832,220; British Pat Nos. 2,003; 27,257; and 350,398; and an article entitled "SEAWEED AS A FERTILIZER" by Ernest Booth appearing in the June 1953 issue of "Organic Gardening" at pages 14–17.

In the process of extracting agar, sodium alginate, carrageenin, and other products from seaweed, various forms of filter cake are produced which are normally discarded and added to the pollution of the environment. Many localities have now forbidden the dumping of such filter cake which are regarded as pollutants and refuse. The present invention not only makes use of such filter cake, but also develops new techniques for obtaining such filter cake and the products formed therefrom.

SUMMARY OF THE INVENTION

The invention provides a product produced by conditioning raw seaweed by mixing the raw seaweed with at least one liquid at least a portion of which is water. This is followed by digesting the conditioned seaweed by cooking the conditioned seaweed with steam, and stirring the steam-cooked conditioned seaweed to form a steam-digested mixture. Thereafter, the filter cake is removed from the top of such steam-digested mixture and is used as the product per se or as the starting material for other products.

An object of the invention is to provide a time-released fertilizer or plant growth stimulator which not only greatly assists the growing of plants, but also replenishes the fertilizer in the surrounding soil.

Another object of the invention is to provide a novel seaweed meal for animal and/or human consumption.

A further object is to provide a time-release fertilizer or plant growth stimulator which includes added quantities of nitrogen and/or phosphorous with a calcium sulfate hemi-hydrate binder.

Another object of the invention is to provide a seaweed extract product for human consumption or medicinal purposes, preferably in the form of edible pills.

Another object of the invention is to combine seaweed filter cake with liquid or solid sodium silicate and/or a calcium sulfate hemi-hydrate binder, for pelletizing or encapsulating, or extruding the resulting product.

A further object of the invention is to provide a time-release fertilizer or plant growth stimulator in the form of cubes, rods, pellets, stakes, or briquets.

Another object of the invention is to provide a seaweed filter cake product having additional amounts of weed killers, insecticides, pesticides, nitrogen, phosphorous, potash, urea, and/or vitamins.

DETAILED DESCRIPTION

There is incorporated herein by reference thereto the entire disclosures of USSN's 550,116 and 550,117 both filed Feb. 14, 1975.

The term "seaweed" as used herein is intended to connote brown seaweed, green seaweed, red seaweed, and all other types of seaweed.

In accordance with the present invention, the starting steps for the production of agar from seaweed may proceed as follows.

The raw seaweed may be a brown seaweed, such as a Phaeophyceae, or a kelp. The raw seaweed is conditioned by placing it in a washing tank where it is washed with a liquid, such as water, to remove the impurities, such as sand and stones. The washed seaweed is then fed to a digester where it will be cooked, using live and indirect steam. Water may be added if desired. The digester may be a machine which will cook and stir the ingredients so that the fibers, the suspended solids, the soluble solids and the liquids become components of a mixture. Certain chemicals may be added to improve the digestion process, if needed.

The digested mixture may then be forced from the digester into a settling tank. Steam pressure may be used to facilitate the mixture transfer. The settling tank may serve as the first stage of the mixture separation, so that the settling tank may serve both as a storage tank and as a separation tank. The settling tank will also allow an evening out of the production process in that the digested mixture may be transferred to the settling tank and thus allow a new batch of seaweed to be loaded into the digester.

From the settling tank, the material will be fed to a blow down tank, and then to one or more desludgers. The desludgers separate the seaweed liquor from the sludge or filter cake. The liquor goes on to further stages for the production of the agar product itself with which the present invention is not primarily concerned.

However, the filter cake or other suspended solid substances coming from the desludger will be conveyed to a dryer for removing a desired portion of the moisture content thereof.

The present invention utilizes the filter cake which can be obtained by various means, such as skimming, desludging, drying, etcetera, at any of the various stages of the process described hereinabove. This filter cake material can be used by itself as a fertilizer or plant growth stimulator or for other purposes, or, as explained in greater detail hereinbelow, may be used as a starting ingredient for the production of other products contemplated by the present invention.

As a further example, there will now be described a process for the production of sodium alginate according to the present invention, at various stages of which process the filter cake may be obtained.

In this example, the raw seaweed may be a brown seaweed such as a kelp. The conditioning of the raw seaweed may be done by a first conditioning machine and a second conditioning machine, with one machine following the other.

The first conditioning machine mixes the raw seaweed with a calcium chloride solution, such as a 1 percent calcium chloride solution, and water. The water may be agitated for certain periods of time and then fed to the second conditioning machine. In the second conditioning machine, there will be added a hydrogen chloride solution, such as a five percent hydrogen chloride solution, and water.

The resultant mixture coming from the second conditioning machine and soda ash, such as four percent soda ash, may now be fed to a digester. The digester will cook and stir the material, and discharge the digested mixture to a settling tank. The material will flow from the settling tank through a blow down tank, and then to an aerator tank and/or to desludgers.

The aerator tank may be supplied with water and compressed air. Some of the material from the blow down tank will be fed directly to the aerator tank, while some of the material from the blow down tank will be fed directly to the desludgers. Some of the material from the aerator tank may be fed to the desludgers, while the remaining material from the aerator tank may be fed directly to a mixing conveyor. Some of the material from the desludgers may be fed to such mixing conveyor, while the remaining material from the desludgers constituting the seaweed liquor will be fed to other stages of the process for producing the alginic acid and sodium alginate with which the present invention is not primarily concerned.

The mixing conveyor mixes the material being fed thereto and conveys it to a pulp dryer, which in turn may feed the dried material to a mill to obtain alginate pulp, which is indicated above as one form of a filter cake with which the present invention is concerned.

A further example in the process for the production of carrageenin in accordance with the present invention will now be described.

The raw seaweed for this process may be red seaweed, such as Irish moss Chondrous Crispus. The raw seaweed is fed to a washer which will take out the impurities, such as sand and stones. The washed or conditioned material may then be fed to a digester, a settling tank, a blow down tank, and to the desludgers, similar to the above description in connection with agar production. The desludgers separate the suspended solids or filter cake from the seaweed liquor. The seaweed liquor is fed to various other stages of the process for obtaining the carrageenin with which the present invention is not primarily concerned.

The filter cake may be fed to a mixing conveyor for feeding to a pulp dryer, which in turn may feed the material to a mill to obtain relatively dry pulp.

The filter cake may be obtained at any of the various stages of the above described processes, or from various stages of other similar processes for the extraction of products from seaweed. The filter cake which has heretofore been discarded and dumped as refuse, can be used as is as a fertilizer or plant growth stimulator, or for other purposes. The invention also contemplates admixing with the filter cake a predetermined quantity of a material selected from the group consisting of vitamins, phosphorous, nitrogen, potash, urea, pesticides, insecticides, and weed killers.

Varius binders may be admixed with the product. For example, a calcium sulfate hemi-hydrate may be used as a binder. A preferable range for the calcium sulfate hemi-hydrate binder is 1 to 26 percent.

Another binder may also be incorporated in the product especially where desired to give strength to the outer surface of the product where, for example, the product is to be pelletized, encapsulated, briquetted, etc. Such a binder may be dry or liquid sodium silicate, although in the preferred embodiments it has been found that spraying liquid sodium silicate is preferred. The sodium silicate is preferably applied in the range of 3 to 6 percent. Some specific examples follow.

As one example, the filter cake is reduced to small particles and admixed with desired quantities of urea, potash and phosphate, and the mixture is passed through a 60 mesh screen. To the mixture there is added 3 percent of a calcium sulfate hemi-hydrate binder. The moisture content of the material as it emanates from the dryer is approximately 45 percent.

Thereafter, the material is pelletized and water is added during the pelletizing process, and while the material is being pelletized it is sprayed with 5 percent of liquid sodium silicate to provide the pellets with a hard outer surface. The moisture content of the material coming from the pelletizer is approximately 60 percent moisture. The pelletized material may then be dried further so that the final product has a 12 percent moisture content.

As a further example, the filter cake is used as is, and has a 42 percent moisture content as it comes from the dryer. The moisture content of the material is reduced to 38 percent after adding approximately 3 percent of a calcium sulfate hemi-hydrate and 5 percent sodium silicate. After pelletization, the moisture content of the material is approximately 60 percent. After further drying, the moisture content of the material is approximately 30 percent.

As another example, the filter cake material coming from the dryer has a moisture content of approximately 47 percent. After nitrogen, potash, and phosphorous are added in the ratio of 8 to 1 to 1, the moisture content of the material is approximately 34 percent. Thereafter, there is added 15 percent of a calcium sulfate hemi-hydrate. The material is then pelletized with the addition of water, but with no sodium silicate being added. After pelletization, the material has a moisture content of approximately 52 percent. The material is then dried so that the moisture content is approximately 21 percent.

In another example, the filter cake material after it is dried has a moisture content of approximately 47 percent. After nitrogen, potash, and phosphorous have been added in the ratio of 5 to 10 to 10, the moisture content of the material is approximately 22 percent. To the material there is then added 10 percent of a calcium sulfate hemi-hydrate, and no sodium silicate. After pelletizing with the addition of water, the moisture content of the material is approximately 51 percent. After subsequent drying, the moisture content of the material is approximately 10 percent.

The calcium sulfate hemi-hydrate binder supplied superior strength, and reduces breakage of the finished pellets and briquets. When this binder is added to a moist mixture, it acts in two ways to provide more durable pellets. First, it improves wet strength by removing water from pellets through chemical combination with moisture after the pellet is formed. Approximately 100 pounds of binder will chemically combine with approximately 17 pounds of water. This action not only improves wet strength of the pellet, making it less subject to breakdown in handling, but actually helps dry the product, thereby reducing fuel requirements. Secondly, when this binder chemically reacts with water, the compound hardens with a cementing action that binds together all the other components of the mixture.

In addition to providing greater strength and hardness, this binder offers a nutritional bonus in the form of biologically - available calcium and sulfate sulfur. This binder is also a low cost source of calcium and sulfate sulfur in fertilizers or plant growth stimulators. It can also be used in pelletized feeds for beef cattle, dairy cows, sheep and other animals to supply supplemental sulfur for maximum feed efficiency. A type of calcium sulfate hemi-hydrate binder is commercially available as BOND-TITE manufactured by the Chemicals Division of the United States Gypsum Company, and attention is directed to United States Gypsum IGL Bulletin No. 225.

The invention also includes pelletizing, extruding, or encapsulating the filter cake or filter cake - derived materials to form coherent masses having any suitable desired shape, such as, for example, pellets, cubes, rods, briquets, silvers, cylinders, pills, oblongs, stakes, or the like.

Also, the novel materials may be used to provide a seaweed meal for animal or human consumption. For example, the material may be used by itself, or may be admixed with conventional grains in order to aid fattening and nutritional digestion of animals and/or humans. The materials may also be used, especially with the binders described above, as a food, a medicine, or a food supplement and preferrably in the form of pills.

The materials may be reduced to particulate or granulated form which is particularly useful for shipping to the location where it is to be employed, and there mixed with a suitable liquid carrier, such as water. The product particles dispersed in the water solution can then be applied to the soil and/or plants.

One of the surprising and unexpected results obtained by the present invention is that when it is employed in its fertilizer or plant growth stimulator or soil conditioner applications, it has been found that previously non-growable soil is converted to readily growable soil which can support vegtation quite easily after application of the product thereto.

Another embodiment of the invention contemplates the use of the material with the binders mentioned above to form very hard stakes or spikes. Such stakes or spikes have sufficient strength to be driven or hit into the ground without fracturing. A series of such stakes may be driven into the ground surrounding a tree or a bush-like plant. Such stakes or spikes are slowly and periodically released with the passage of time into the adjacent soil and ultimately into the tree in question.

I claim:

1. A product produced by:
    conditioning raw seaweed by mixing said raw seaweed with at least one liquid at least a portion of which is water
    wherein said raw seaweed is conditioned by a first conditioning machine and by a second conditioning machine;
    in said first conditioning machine said raw seaweed is mixed with a calcium chloride solution and water, and is agitated for predetermined periods of time and the resulting mixture is then fed to said second conditioning machine;
    in said second conditioning machine there is added to the mixture a hydrogen chloride solution and water;
    the resulting mixture is then fed to the apparatus for performing said digesting where it is admixed with soda ash;
    the soda ash and twice-conditioned seaweed mixture is digested by cooking with steam, and stirring the steam-cooked soda ash and twice-conditioned mixture to form a steam-digested mixture; and
    the filter cake is removed from the top of the resulting steam-digested mixture and is used as the product per se.

2. A product produced according to claim 1, wherein:
    the digested mixture from said digesting step is fed to a settling tank, and from there through a blow down tank, and then to an aerator tank and/or to desludgers;
    suspended solid substances coming from the aerator and from the desludgers are conveyed to a dryer, and the resulting material coming from the dryer is used as the product per se.

3. A product accordint to claim 2, wherein: the product contains no more than a trace of alginic acid.

4. A product according to claim 2, wherein:
    there is admixed with the product a predetermined quantity of a material selected from the group consisting of weed killers, insecticides, pesticides, nitrogen, phosphorous, potash, and vitamins.

5. A product according to claim 2, wherein:
    said filter cake or said product is dried to a first predetermined moisture content; and
    the resulting dried material is admixed with sodium silicate and/or calcium sulfate hemi-hydrate as binders.

6. A product according to claim 2, wherein:
    said filter cake or said product is admixed with from 1 to 26 percent of a calcium sulfate hemi-hydrate and/or 1 to 10 percent of sodium silicate.

7. A product according to claim 2, wherein:
    said filter cake or said product is first dried to have a moisture content in the range of 35 to 50 percent moisture;
    thereafter the dried material is pelletized while adding water thereto so that the resulting material has a moisture content in the range of 45 to 70 percent moisture; and
    thereafter the material is further dried so that the resulting product has a moisture content in the range of 8 to 35 percent moisture.

8. A product according to claim 2, wherein:
    the product is admixed with a liquid carrier therefor to produce a liquid concentrate thereof for utilization as a fertilizer, soil conditioner, or food or meal for the consumption of animals and/or human beings.

9. A product produced according to claim 2, wherein:
    the filter cake is removed from the top of the mixture in said aerator tank and/or desludgers.

10. A product according to claim 9, wherein:
    the product contains no more than a trace of alginic acid.

11. A product according to claim 9, wherein:
    there is admixed with the product a predetermined quantity of a material selected from the group consisting of weed killers, insecticides, pesticides, nitrogen, phosphorous, potash, and vitamins.

12. A product according to claim 9, wherein:
said filter cake or said product is dried to a first predetermined moisture content; and
the resulting dried material is admixed with sodium silicate and/or calcium sulfate hemi-hydrate as binders.

13. A product according to claim 9, wherein:
said filter cake or said product is admixed with from 1 to 26 percent of a calcium sulfate hemi-hydrate and/or 1 to 10 percent of sodium silicate.

14. A product according to claim 9, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

15. A product according to claim 9, wherein:
the product is admixed with a liquid carrier therefor to produce a liquid concentrate thereof for utilization as a fertilizer, soil conditioner, or food or meal for the consumption of animals and/or human beings.

16. A product according to claim 1, wherein:
the product contains no more than a trace of alginic acid.

17. A product according to claim 16, wherein:
there is admixed with the product a predetermined quantity of a material selected from the group consisting of weed killers, insecticides, pesticides, nitrogen, phosphorous, potash, and vitamins.

18. A product according to claim 16, wherein:
said filter cake or said product is dried to a first predetermined moisture content; and
the resulting dried material is admixed with sodium silicate and/or calcium sulfate hemi-hydrate as binders.

19. A product according to claim 16, wherein:
said filter cake or said product is admixed with from 1 to 26 percent of a calcium sulfate hemi-hydrate and/or 1 to 10 percent of sodium silicate.

20. A product according to claim 16, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

21. A product according to claim 16, wherein:
the product is admixed with a liquid carrier therefor to produce a liquid concentrate thereof for utilization as a fertilizer, soil conditioner, or food or meal for the consumption of animals and/or human beings.

22. A product according to claim 1, wherein:
there is admixed with the product a predetermined quantity of a material selected from the group consisting of weed killers, insecticides, pesticides, nitrogen, phosphorous, potash, and vitamins.

23. A product according to claim 22, wherein:
said filter cake or said product is dried to a first predetermined moisture content; and
the resulting dried material is admixed with sodium silicate and/or calcium sulfate hemi-hydrate as binders.

24. A product according to claim 22, wherein:
said filter cake or said product is admixed with from 1 to 26 percent of a calcium sulfate hemi-hydrate and/or 1 to 10 percent of sodium silicate.

25. A product according to claim 22, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

26. A product according to claim 22, wherein:
the product is admixed with a liquid carrier therefor to produce a liquid concentrate thereof for utilization as a fertilizer, soil conditioner, or food or meal for the consumption of animals and/or human beings.

27. A product according to claim 1, wherein:
said filter cake or said product is dried to a first predetermined moisture content; and
the resulting dried material is admixed with sodium silicate and/or calcium sulfate hemi-hydrate as binders.

28. A product according to claim 27, wherein:
said filter cake or said product is admixed with from 1 to 26 percent of a calcium sulfate hemi-hydrate and/or 1 to 10 percent of sodium silicate.

29. A product according to claim 27, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

30. A product according to claim 27, wherein:
the product is admixed with a liquid carrier therefor to produce a liquid concentrate thereof for utilization as a fertilizer, soil conditioner, or food or meal for the consumption of animals and/or human beings.

31. A product according to claim 1, wherein:
said filter cake or said product is admixed with from 1 to 26 percent of a calcium sulfate hemi-hydrate and/or 1 to 10 percent of sodium silicate.

32. A product according to claim 31, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and thereafter the material is further dried so that the resulting product has a moisture content in the range of 8 to 35 percent moisture.

33. A product according to claim 31, wherein:
the product is admixed with a liquid carrier therefor to produce a liquid concentrate thereof for utilization as a fertilizer, soil conditioner, or food or meal for the consumption of animals and/or human beings.

34. A product according to claim 1, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

35. A product according to claim 34, wherein:
the product is admixed with a liquid carrier therefor to produce a liquid concentrate thereof for utilization as a fertilizer, soil conditioner, or food or meal for the consumption of animals, and/or human beings.

36. A product according to claim 1, wherein:
the product is admixed with a liquid carrier therefor to produce a liquid concentrate thereof for utilization as a fertilizer, soil conditioner, or food or meal for the consumption of animals and/or human beings.

37. A product according to claim 1, wherein:
the product contains no more than a trace of alginic acid.

38. A product according to claim 1, wherein:
there is admixed with the product of a predetermined quantity of material selected from the group consisting of weed killers, insecticides, pesticides, nitrogen, phosphorous, potash, and vitamins.

39. A product according to claim 1, wherein:
said filter cake or said product is dried to a first predetermined moisture content; and
the resulting dried material is admixed with sodium silicate and/or calcium sulfate hemi-hydrate as binders.

40. A product according to claim 1, wherein:
said filter cake or said product is admixed with from 1 to 26 percent of a calcium sulfate hemi-hydrate and/or 1 to 10 percent of sodium silicate.

41. A product according to claim 1, wherein:
said filter cake or said product is first dried to have a moisture content in the range of 35 to 50 percent moisture;
thereafter the dried material is pelletized while adding water thereto so that the resulting material has a moisture content in the range of 45 to 70 percent moisture; and
thereafter the material is further dried so that the resulting product has a moisture content in the range of 8 to 35 percent moisture.

42. A product according to claim 1, wherein:
the product is admixed with a liquid carrier therefor to produce a liquid concentrate thereof for utilization as a fertilizer, soil conditioner, or food or meal for the consumption of animals and/or human beings.

* * * * *